(12) United States Patent
Higaki et al.

(10) Patent No.: US 7,077,830 B2
(45) Date of Patent: Jul. 18, 2006

(54) MEDICAL SYRINGE NEEDLE

(75) Inventors: Yoshio Higaki, Osaka (JP); Kenji Yashiro, Osaka (JP); Mitsuo Murakami, Osaka (JP); Toshio Tochiyama, Osaka (JP)

(73) Assignee: Nipro Corporation, Osaka (JP)

( * ) Notice: Subject to any disclaimer, the term of this patent is extended or adjusted under 35 U.S.C. 154(b) by 50 days.

(21) Appl. No.: 10/239,162

(22) PCT Filed: Mar. 12, 2001

(86) PCT No.: PCT/JP01/01927

§ 371 (c)(1),
(2), (4) Date: Sep. 20, 2002

(87) PCT Pub. No.: WO01/70312

PCT Pub. Date: Sep. 27, 2001

(65) Prior Publication Data

US 2003/0045839 A1    Mar. 6, 2003

(30) Foreign Application Priority Data

Mar. 22, 2000  (JP) ............................ 2000-079403

(51) Int. Cl.
*A61M 5/32* (2006.01)
*A61M 37/00* (2006.01)
*A61M 5/31* (2006.01)
*A61B 19/00* (2006.01)

(52) U.S. Cl. ...................... 604/272; 604/6.16; 604/240; 604/413

(58) Field of Classification Search ............... 604/6.15, 604/6.16, 93.01, 263, 272, 523, 411, 412, 604/413, 240, 264, 533, 534, 535
See application file for complete search history.

(56) References Cited

U.S. PATENT DOCUMENTS

| 2,211,537 A | 8/1940 | Dickinson |
| 3,186,408 A | 6/1965 | Jacobs |
| 3,994,295 A * | 11/1976 | Wulff ......................... 604/241 |
| 4,040,421 A | 8/1977 | Young |
| 4,121,588 A | 10/1978 | Geiger |

(Continued)

FOREIGN PATENT DOCUMENTS

EP    0 824 926 A2    2/1998

(Continued)

*Primary Examiner*—Michael J. Hayes
*Assistant Examiner*—Mark K Han
(74) *Attorney, Agent, or Firm*—Birch, Stewart, Kolasch and Birch, LLP

(57) ABSTRACT

A needle for medical use, which is free from breakage of a cannula even if subjected to reapeated bending operations or puncture into the root of teeth in use. The needle is charactrized in that a cannula (2) is fixed to a hub (1) by charging a bonding adhesive in an adhesive-filling portion (11) provided in a distal end of the hub (1) so that a root (21) of the cannula (2) is located below the distal end (121) of the hub (1). The distal end of the hub (1) may be formed into a configuration provided with an annular rib (12) extending axially and surrounding the adhesive-filling portion (11).

18 Claims, 5 Drawing Sheets

U.S. PATENT DOCUMENTS

| | | | | |
|---|---|---|---|---|
| 4,240,425 A | * | 12/1980 | Akhavi | 604/199 |
| 4,240,426 A | * | 12/1980 | Akhavi | 604/243 |
| 4,249,530 A | * | 2/1981 | Millet | 604/192 |
| 4,995,870 A | * | 2/1991 | Baskas | 604/110 |
| 5,024,659 A | * | 6/1991 | Sjostrom | 604/110 |
| 5,360,423 A | * | 11/1994 | McCormick | 604/403 |
| 5,405,330 A | * | 4/1995 | Zunitch et al. | 604/240 |
| 6,585,701 B1 | * | 7/2003 | Dysarz | 604/263 |
| 6,595,960 B1 | * | 7/2003 | West et al. | 604/181 |

FOREIGN PATENT DOCUMENTS

| | | |
|---|---|---|
| FR | 2 785 813 A1 | 5/2000 |
| JP | 58-54848 U | 4/1983 |

* cited by examiner

<At the time of pressing>
Press a cannula with a thumb while holding a barrel of a syringe for conduction anesthesia.

<At the time of restoring>
Press a cannula back with a thumb while holding a barrel of a syringe for conduction anesthesia.

BACKGROUND ART

MEDICAL SYRINGE NEEDLE

This application is the national phase under 35 U.S.C. § 371 of PCT International Application No. PCT/JP01/01927 which has an International filing date of Mar. 12, 2001, which designated the United States of America.

BACKGROUND ART

The present invention relates to a needle for medical use comprising an easily bendable cannula which has a small diameter and a thin wall. The needle for medical use of the present invention is suitable as a dental needle used for local anesthesia in dental treatment or a needle used for delivery of insulin.

In dental treatment, dental needles have generally been used to inject an anesthetic agent into a dental root. In this case, it is general practice to bend a cannula from the root thereof to a suitable angle just before use of needle since the needle cannot be guided to a site of injection as it is because of a small oral cavity prevent.

However, such a needle involves a danger of causing breakage of the cannula at the time of sticking the needle into the dental root. Further, the above bending operation is often applied two or more times to the needle used for the identical patient, so that the cannula breaks at the root during the bending operation of the needle before the medical treatment.

On the other hand, needles for delivery of insulin comprise a cannula which has a small diameter and a thin wall. For this reason, the needles have such a problem that the cannulae are often broken in use (i.e., at the time of puncture or removal of the needle) because of a matter of procedure, probably, incorrect puncture of the needle.

In view of the above circumstances, the present invention has been made and an object of the invention is to provide a needle for medical use which is free from breakage of the cannula even if subjected to repeated bending operation or puncture into root of teeth in use. Another object of the present invention is to provide a needle for medical use, which is free from breakage of cannula owing to a matter of procedure.

DISCLOSURE OF INVENTION

The inventors have investigated causes of needle breakage to overcome the above problems and the following became clear. In case of the conventional dental needle as shown in FIG. 4, the bending operation of a cannula 20 by a dentist is carried out by pressing a cannula 20 with a dentist's thumb F after fitting the needle N on a syringe body S, as illustrated in FIG. 3. In this case, the cannula 20 is unexceptionally bent at a position where the cannula 20 is in contact with a surface of a bonding adhesive layer 105, i.e., at a root 201 of the cannula. Further, the cannula 20 is broken at the root 201 of the cannula 20 without exception. Also it has been found that in case of conventional needles for delivery of insulin as shown in FIG. 5, most of the cannulae are broken at a portion of a bonding adhesive. A solution of the above problems was hit upon by these facts and the present invention has been completed on the basis of idea that the above problems would be overcome by preventing the force from being applied directly to the root of the cannula.

Accordingly, a needle for medical use of the present invention is characterized in that a cannula is fixed to a hub with a bonding adhesive charged in an adhesive-filling portion provided in a distal end of the hub so that a root of the cannula is located at a position below the distal end of the hub. In this case, it is preferred that the root of cannula is located at a distance of at least 1 mm below the distal end of the hub. In the meantime, the hub may be provided with an axially extending annular rib which surrounds the adhesive-filling portion, and the root of the cannula may be located at a position below the distal end of the annular rib. In this case, it is preferred to set a height of the annular rib from the root of cannula to 1 mm or more.

BEST MODE FOR CARRYING OUT THE INVENTION

Embodiments of the invention will be explained below on the basis of the accompanying drawings.

Figure 1:
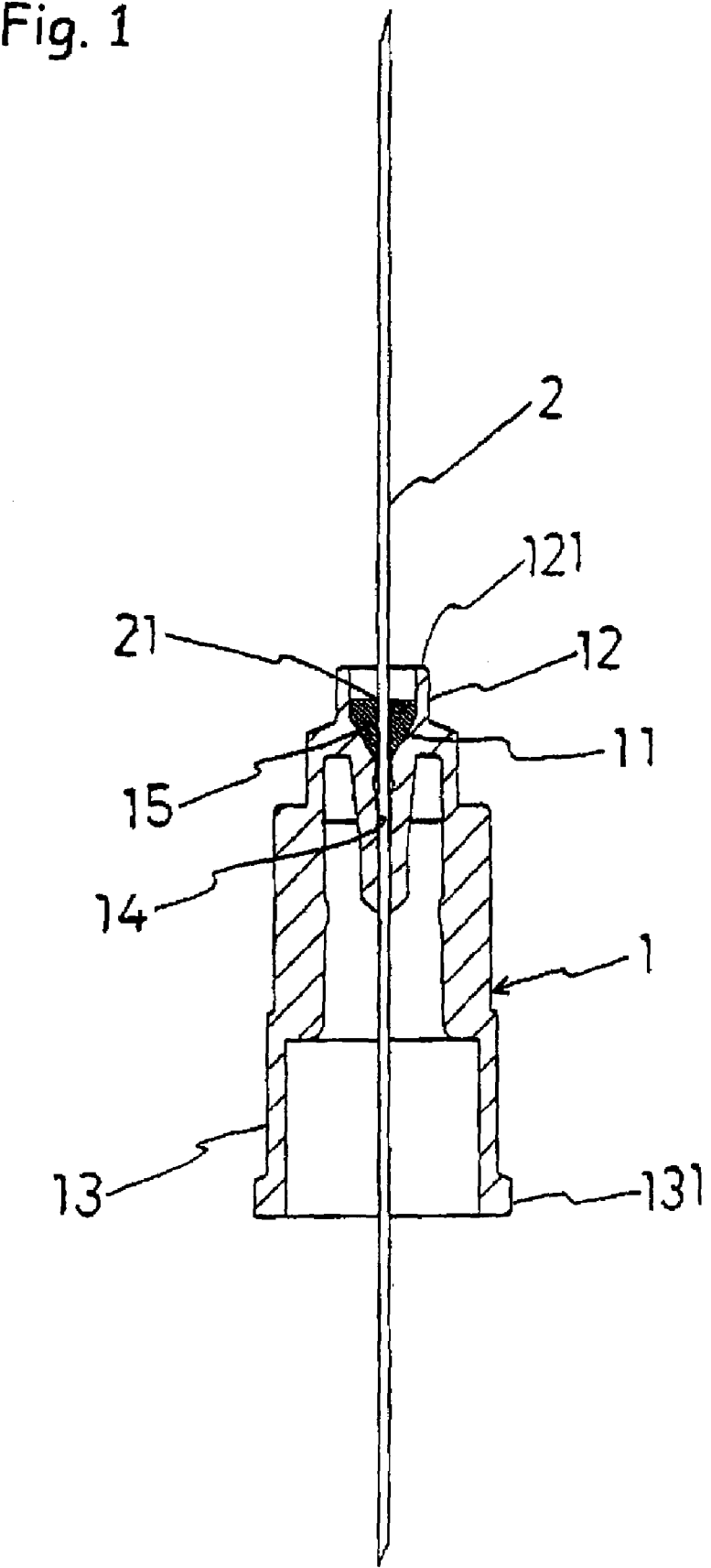
FIG. 1 is a longitudinal section of a needle illustrating one embodiment of the present invention.
Figure 2:
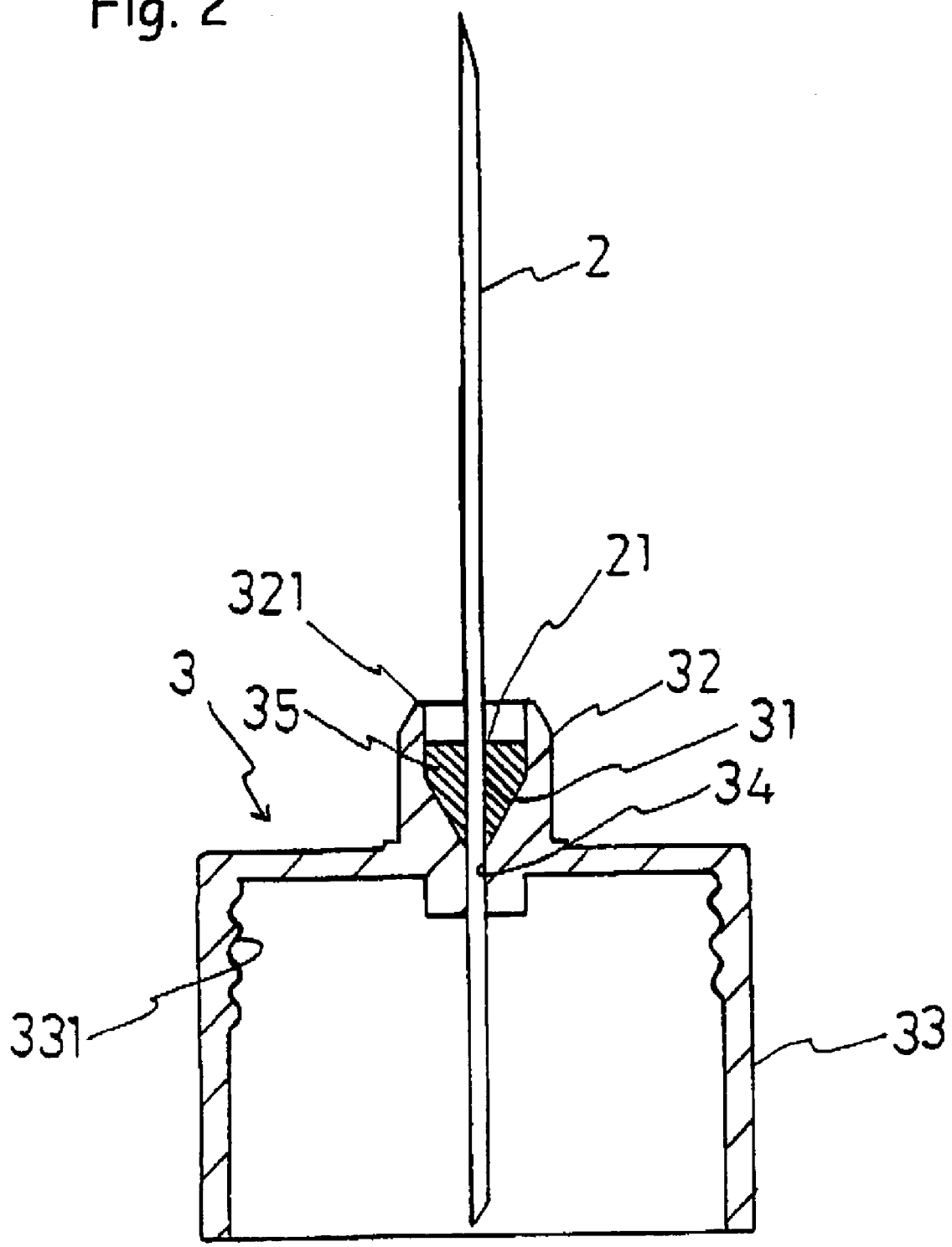
FIG. 2 is a vertical cross section illustrating another embodiment of the present invention.

As illustrated in FIGS. 1 and 2, a needle for medical use is characterized in that a cannula 2 is fixed to a hub 1, 3 by charging a bonding adhesive in an adhesive-filling portion 11, 31 provided in a distal end of the hub 1, 3, so that a root 21 of the cannula 2 is located below the distal end 121, 321 of the hub 1, 3. The distal end of the hub 1, 3 may be formed into a configuration provided with an annular rib 12, 32 extending axially and surrounding the adhesive-filling portion 11, 31. In this case, the root 21 of the cannula 2 is located below the distal end 121, 321 of the annular rib 12, 32.

FIG. 1 shows one embodiment of the dental needle. The hub 1 is generally made of a transparent thermoplastic resin such as polyethylene, polypropylene and the like. The hub 1 is provided at a proximal end thereof with an engaging portion 13 for engagement with a tip of a syringe (not shown) and at a distal end thereof with an adhesive-filling portion 11 to be charged with a bonding adhesive. The engaging portion 13 is provided at a proximal end thereof with a double-threaded screw 131 as an engaging means and at a central portion thereof with an axial through-hole 14 passing therethrough for insertion of the cannula 2.

The cannula 2 is inserted into the through-hole 14 and fixed to the hub 1 with the bonding adhesive charged into the adhesive-filling portion 11 of the hub 1. Points of contact between the surface of the bonding adhesive layer 15 and the cannula 2, i.e., a root 21 of the cannula 2 is located at a position below the distal end 121 of the hub 1. Thus, when the cannula 2 is pressed with the thumb to bend it, there is a certain distance between a power point (a portion pressed by a finger) and a supporting point (root 21 of the cannula 2). For this reason, the force applied to the root of the cannula 2 is reduced by deflection of the cannula 2. As a result, the cannula 2 is difficult to be broken.

As illustrated in FIG. 1, the distal portion of the hub 1 may be formed into a configuration provided with an annular rib 12 extending axially and surrounding an adhesive-filling portion 11. In such a case, the distal end 121 of the hub 1 shall read "the distal end of the annular rib 12" and the preferable height of the annular rib 12 from the root 21 of the cannula 2 shall read at least 1 mm.

EXAMPLES 1–3

There were prepared sets of ten samples with dimensions of 30 G×21 mm for each kind of the dental needle of the present invention (Example 1), the conventional dental needle (Comparative example 1), and dental needles prepared by cutting off each annular rib of example 1 with a cutter (comparative example 2). The samples were then subjected to a repeated flexural strength test. The results obtained are shown in Table 1. The dental needles of Example 1 have an annular rib with a height of 1.50±0.41 mm from the root of cannula.

Figure 3A:
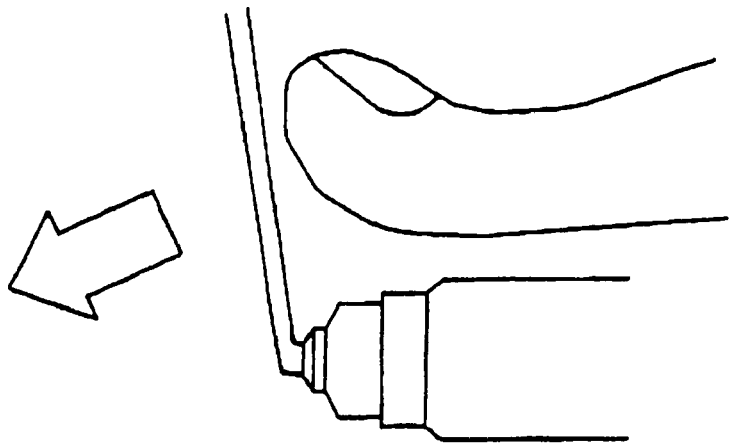
FIG. 3 is a schematic diagram illustrating a repeated bending strength test of cannula, which includes the steps of (a) bending the cannula one side with a thumb and then (b) returning it to the original state.
Figure 3B:
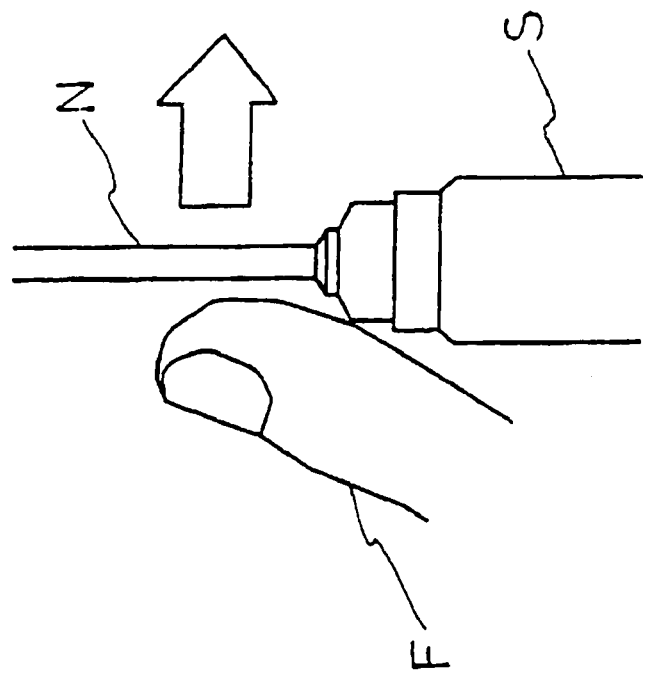
Figure 4:
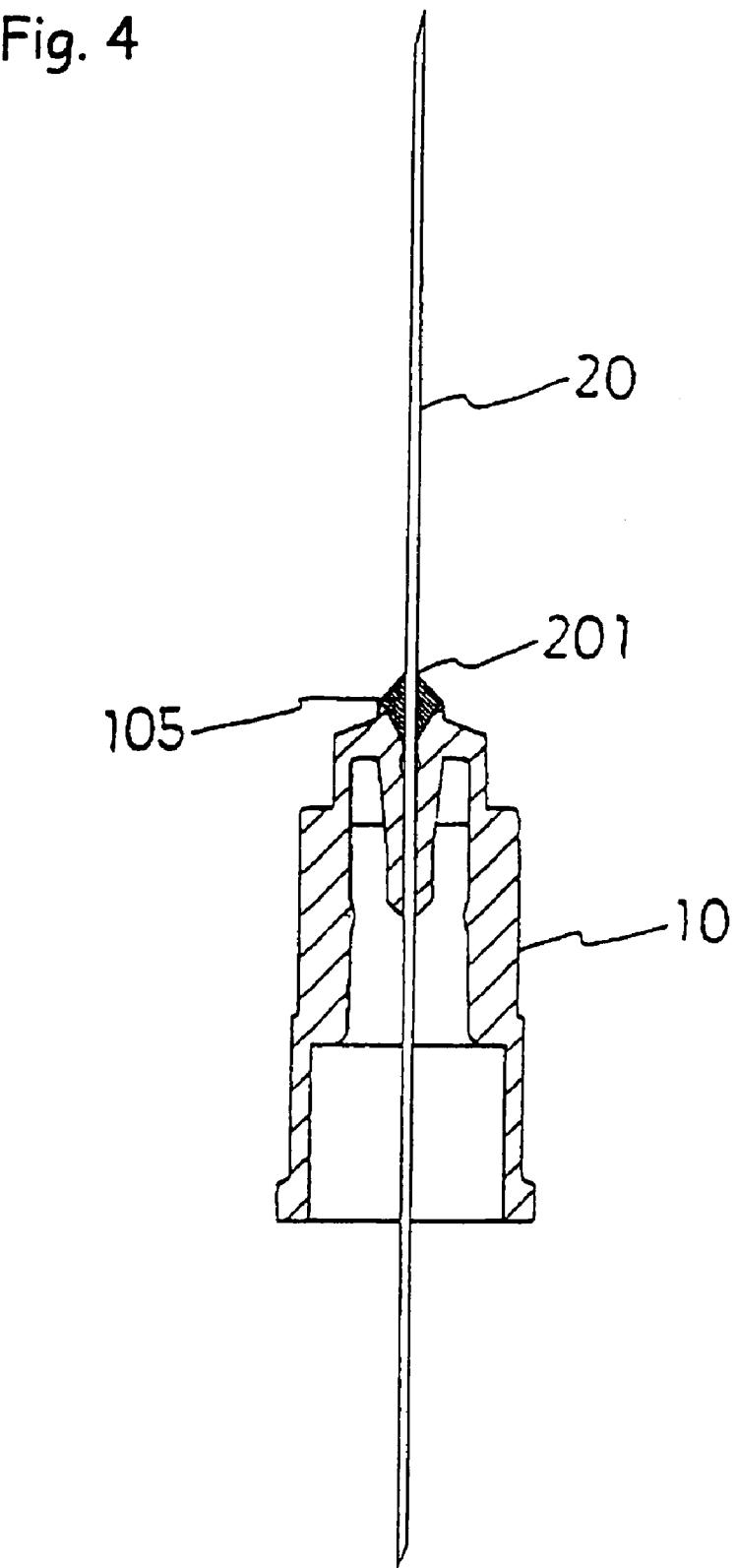
FIG. 4 is a longitudinal section of a conventional dental needle.
Figure 5:
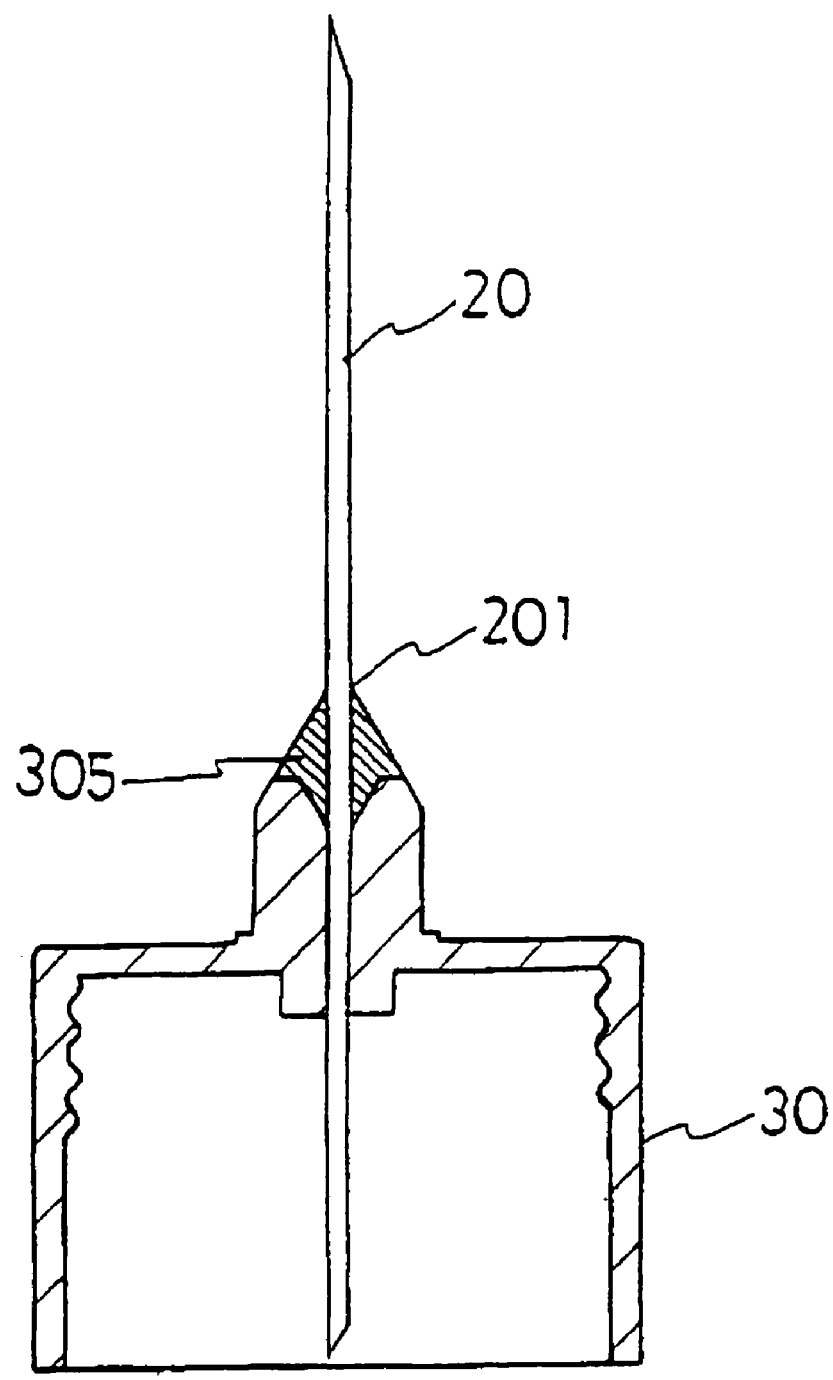
FIG. 5 is a vertical cross section illustrating conventional needle for insulin injection.

The test was carried out by fixing a needle to a syringe for conduction anesthesia, and repeating operations of bending the cannula to one side with a thumb and restoring the bent needle to its original state until the cannula is broken (q.v. FIG. 3). A bending angle of the cannula is set to 25°, 45°, 60° or 90° and each numerical value in the table is the number of repeated bending till the cannula is broken.

TABLE 1

| Bending angle | 25° | 45° | 60° | 90° |
|---|---|---|---|---|
| Example 1 | 35.25 ± 5.04 | 18.90 ± 1.88 | 11.10 ± 1.18 | 6.60 ± 1.24 |
| Comp ex. 1 | 9.00 ± 0.84 | 4.80 ± 0.56 | 3.20 ± 0.24 | 1.00 ± 0.22 |
| Comp ex. 2 | 10.30 ± 1.27 | 5.30 ± 0.68 | 3.20 ± 0.46 | 2.40 ± 0.37 |

From the result of Table 1, it can be seen that the needle of the present invention is much improved in repeated flexural strength as compared with the conventional needles. Although the needle of comparative example 2 shows somewhat improved flexural strength, this would result from the fact that the surface of the adhesive is flattened or slightly caved and thus some distance exists between the power point and the supporting point.

FIG. 2 shows an example of a needle for delivery of insulin. As with the above dental needle, a hub 3 is generally made of a thermoplastic resin such as polyethylene, polypropylene and the like and colored in most cases. The hub 3 is provided at a proximal end thereof with an engaging portion 33 for engagement with a tip of a syringe (not shown), and at a distal end thereof with an adhesive-filling portion 31 to be filled with a bonding adhesive. The engaging portion 33 is provided on a distal side thereof with female screw 331 serving as engaging means. The hub 31 is provided on the central axis thereof with an axial through-hole 34 for insertion of cannula, which passes through the hub 3. A cannula 2 is fitted in the through-hole 34 and fixed to the hub 3 with a bonding adhesive applied to the adhesive-filling portion 31.

Points of contact between the surface of the bonding adhesive layer 35 and the cannula 2, i.e., a root 21 of the cannula 2 is located at a position below the distal end 321 of the hub 3. Thus, when the cannula 2 is bent, there is a certain distance between a power point and a supporting point (root 21 of the cannula 2). For this reason, the force applied to the root 21 of the cannula 2 is reduced by deflection of the cannula 2 and thus the cannula 2 is difficult to be broken.

As illustrated in FIG. 2, the distal portion of the hub 3 may be formed into a configuration provided with an axially extending annular rib 32 so as to surround the adhesive-filling portion 31. In such a case, "the distal end 321 of the hub 3" shall read "the distal end of the annular rib 32", while "the height of the annular rib from the root of cannula is 1 mm or more" shall read "the height of the annular rib 32 from the root 21 of the cannula 2 is at least 1 mm".

EXAMPLES 4–5

There were prepared sets of ten samples with dimensions of 30 G×21 mm for each kind of the needle for delivery of insulin of the present invention (Example 2) and conventional insulin needle (Comparative example 3). The samples were then subjected to the flexural strength test as with the above dental needles (FIG. 3). The results obtained were shown in Table 2. The average height of the annular rib from the root of cannula was 1.49±0.23 mm.

From Table 1, it can be seen that the repeated flexural strength is much improved as compared with the conventional needles.

TABLE 2

| Bending angle | 25° | 45° | 60° | 90° |
|---|---|---|---|---|
| Example 2 | 12.65 ± 1.51 | 7.13 ± 0.70 | 4.65 ± 0.52 | 1.78 ± 0.34 |
| Comp ex. 3 | 4.33 ± 0.88 | 2.98 ± 0.41 | 1.90 ± 0.38 | 1.23 ± 0.26 |

INDUSTRIAL APPLICABILITY

As will be understood from the above description, the needle for medical use of the present invention is so configured that the root of the cannula is located below the distal end of the hub. Thus, the cannula flexes when pressed by a finger since there is a certain distance between a power point and supporting point of the cannula. Accordingly, it is possible to prevent the cannula from breakage due to repeated bending operations or puncture of injecting site in use.

The invention claimed is:

1. A needle for medical use comprising:
   a hub;
   an adhesive-filling portion provided in a distal portion of the hub; and
   a bonding adhesive charged into a proximal portion of the adhesive-filling portion while leaving a distal portion of the adhesive-filling portion uncharged, an exposed surface of the bonding adhesive being located inside the adhesive-filling portion of the hub and being separated from a distal end of the hub by a predetermined distance;
   a cannula having a small diameter and a thin wall, said cannula having a central portion that is fixed to the hub by the bonding adhesive, a root located at the exposed surface of the bonding adhesive, and an exposed distal portion beginning at the root and extending in the distal direction from the exposed surface of the bonding adhesive, the exposed distal portion being easily bendable.

2. The needle according to claim 1, wherein said hub is provided at the distal end thereof with an axially extending annular rib surrounding the adhesive-filling portion so that the root of the cannula is located at a position below the distal end of the annular rib.

3. The needle according to claim 2, wherein the root of said cannula is located at a distance of 1 mm or more below from the distal end of the hub.

4. The needle according to claim 2, wherein at least a portion of an inner side wall and at least a portion of an outer side wall of the axially extending annular rib on the distal end of the hub are cylindrical-shaped.

5. The needle according to claim 1, wherein a proximal end of the adhesive-filling portion is conical-shaped.

6. The needle according to claim 1, wherein a surface of the adhesive is flattened or caved.

7. A dental needle comprising:
a hub;
an adhesive-filling portion provided in a distal portion of the hub; and
a bonding adhesive charged into a proximal portion of the adhesive-filling portion while leaving a distal portion of the adhesive-filling portion uncharged, an exposed surface of the bonding adhesive being located inside the adhesive-filling portion of the hub and being separated from a distal end of the hub by a predetermined distance;
a cannula having a small diameter and a thin wall, said cannula having a central portion that is fixed to the hub by the bonding adhesive, a root located at the exposed surface of the bonding adhesive, and an exposed distal portion beginning at the root and extending in the distal direction from the exposed surface of the bonding adhesive, the exposed distal portion being easily bendable.

8. The needle according to claim 7, wherein said hub is provided at the distal end thereof with an axially extending annular rib surrounding the adhesive-filling portion, and wherein the root of the cannula is located below the distal end of the annular rib.

9. The needle according to claim 8, wherein the root of said cannula is located at a distance of 1 mm or more below from the distal end of the hub.

10. The needle according to claim 8, wherein at least a portion of an inner side wall and at least a portion of an outer side wall of the axially extending annular rib on the distal end of the hub are cylindrical-shaped.

11. The needle according to claim 7, wherein a proximal end of the adhesive-filling portion is conical-shaped.

12. The needle according to claim 7, wherein a surface of the adhesive is flattened or caved.

13. A needle for delivery of insulin, comprising:
a hub;
an adhesive-filling portion provided in a distal portion of the hub; and
a bonding adhesive charged into a proximal portion of the adhesive-filling portion while leaving a distal portion of the adhesive-filling portion uncharged, an exposed surface of the bonding adhesive being located inside the adhesive-filling portion of the hub and being separated from a distal end of the hub by a predetermined distance;
a cannula having a small diameter and a thin wall, said cannula having a central portion that is fixed to the hub by the bonding adhesive, a root located at the exposed surface of the bonding adhesive, and an exposed distal portion beginning at the root and extending in the distal direction from the exposed surface of the bonding adhesive, the exposed distal portion being easily bendable.

14. The needle according to claim 13, wherein said hub is provided at the distal end thereof with an axially extending annular rib surrounding the adhesive-filling portion, and wherein the root of the cannula is located below the distal end of the annular rib.

15. The needle according to claim 14, wherein the root of said cannula is located at a distance of 1 mm or more below from the distal end of the hub.

16. The needle according to claim 14, wherein at least a portion of an inner side wall and at least a portion of an outer side wall of the axially extending annular rib on the distal end of the hub are cylindrical-shaped.

17. The needle according to claim 13, wherein a proximal end of the adhesive-filling portion is conical-shaped.

18. The needle according to claim 13, wherein a surface of the adhesive is flattened or caved.

* * * * *